US011033602B2

(12) United States Patent
Bencic

(10) Patent No.: US 11,033,602 B2
(45) Date of Patent: Jun. 15, 2021

(54) INHALATION DEVICE

(71) Applicant: XELLIA PHARMACEUTICALS APS, Copenhagen (DK)

(72) Inventor: Nenad Bencic, Zagreb (HR)

(73) Assignee: XELLIA PHARMACEUTICALS APS, Copenhagen (DK)

(*) Notice: Subject to any disclaimer, the term of this patent is extended or adjusted under 35 U.S.C. 154(b) by 0 days.

(21) Appl. No.: 15/516,286

(22) PCT Filed: Oct. 1, 2015

(86) PCT No.: PCT/EP2015/072736
§ 371 (c)(1),
(2) Date: Mar. 31, 2017

(87) PCT Pub. No.: WO2016/050933
PCT Pub. Date: Apr. 7, 2016

(65) Prior Publication Data
US 2019/0022171 A1    Jan. 24, 2019

Related U.S. Application Data

(60) Provisional application No. 62/059,748, filed on Oct. 3, 2014.

(51) Int. Cl.
*A61K 38/12*    (2006.01)
*A61K 9/00*    (2006.01)
*A61K 9/08*    (2006.01)
*A61M 11/00*    (2006.01)
*A61M 15/00*    (2006.01)

(52) U.S. Cl.
CPC ............ *A61K 38/12* (2013.01); *A61K 9/0078* (2013.01); *A61K 9/08* (2013.01); *A61M 11/003* (2014.02); *A61M 11/00* (2013.01); *A61M 15/00* (2013.01); *Y02A 50/30* (2018.01)

(58) Field of Classification Search
CPC ...................................................... A61K 38/12
See application file for complete search history.

(56) References Cited

U.S. PATENT DOCUMENTS

| 3,317,506 | A | 5/1967 | Wilkinson | |
| 5,767,068 | A * | 6/1998 | VanDevanter | ......... A61K 38/12 424/499 |
| 10,532,080 | B2 * | 1/2020 | Bencic | ................. A61P 31/04 |
| 2003/0143162 | A1 | 7/2003 | Speirs et al. | |
| 2004/0022740 | A1 | 2/2004 | Baker et al. | |
| 2008/0066739 | A1 | 3/2008 | LeMahieu et al. | |
| 2009/0215677 | A1 * | 8/2009 | Vaara | ..................... C07K 7/62 514/1.1 |
| 2012/0316105 | A1 | 12/2012 | Magee et al. | |
| 2016/0002296 | A1 | 7/2016 | Gunnes et al. | |
| 2017/0218024 | A1 | 8/2017 | Bjornstad | |
| 2017/0239321 | A1 | 8/2017 | Bencic | |

FOREIGN PATENT DOCUMENTS

| CN | 102531955 A | 7/2012 |
| DE | 1906699 A1 | 2/1970 |
| EP | 1752161 A2 | 2/2007 |
| FR | 1586834 A | 3/1970 |
| RU | 2712276 C2 | 1/2020 |
| WO | 19890009626 A1 | 10/1989 |
| WO | 199820836 | 5/1998 |
| WO | 2008025560 A1 | 3/2008 |
| WO | 2011051070 A1 | 5/2011 |
| WO | 2012168820 A1 | 12/2012 |
| WO | 2014108469 A1 | 7/2014 |
| WO | 2014195405 A1 | 12/2014 |

OTHER PUBLICATIONS

Brochet et al., 2007, Comparative efficacy of two doses of nebulized colistimethate for the eradication of Pseudomonas aeruginosa in children with cystic fibrosis, Can Respir J, 14(8): 473-479.*
Yapa et al., May 2014, Pulmonary and Systemic Pharmacokinetics of inhaled and Intravenous Colistin Methanesulfonate in Cystic Fibrosis Patients: Targeting Advantage of Inhalation Administration, Antimicrobial Agents and Chemotherapy, 58(5): 2570-2579.*
Li et al., 2006, Colistin: the re-emerging antibiotic for multidrug-resistant Gram-negative bacterial infections, Lancet Infect Dis, 6: 589-601.*
Kassamali et al.; "Polymyxins: Wisdom Does Not Always Come With Age"; Clinical Infectious Diseases; 57; pp. (2013) 877-883; (2013).
Athanassa et al.; "Pharmacokinetics of Inhaled Colistimethate Sodium (CMS) in Mechanically Ventilated Critically Ill Patients"; Intensive Care Med 38; pp. 1779-1786; (2012).
BioPharm International Editors; "Biopharmaceutical Manufacturing Using Blow-Fill-Seal Technology"; in BioPharm International; 24(7); 7 pages; (2011).
Keller et al.; "Performance Characteristics of Colistimethate Sodium Solutions (Colistin) Delivered by Jet Nebulizers Compared to the eFlow SCF Electronic Nebulizer"; North American Cystic Fibrosis Conference, St. Louis, USA, Oct. 14-17, (2004).
International Search Report and Written Opinion; International Application No. PCT/EP20151072736; International Filing Date Oct. 1, 2015; dated Nov. 23, 2015; 14 pages.
Kamin et al.; "Inhalation Solutions—which one are allowed to be mixed? Physico-chemical Coompatibility of Drug Solutions in Nebulizers"; Journal of Cystic Fibrosis; 5; pp. 205-213; (2006).
Li et al; "Defining the Dosage Units for Colistin Methanesulfonate: Urgent Need for International Harmonization"; Antimicrobial Agents and Chemotherapy; 50(12); pp. 4231-4232; (2006).
Young et al.; "Optimization of Anti-Pseudomonal Antibiotics for Cystic Fibrosis Pulmonary Exacerbations: IV. Colistimethate Sodium"; Pediatric Pulmonology; 48; pp. 1-7; (2013).

(Continued)

*Primary Examiner* — Amber D Steele
(74) *Attorney, Agent, or Firm* — Cantor Colburn LLP

(57) ABSTRACT

Disclosed herein is a pulmonary administration device, comprising a spray nozzle unit and a cartridge containing an aqueous solution comprising from 70 to 400 mg A/m L of a sulfomethylated polymyxin, and use of sulfomethylated polymyxin in a device for pulmonary administration in a patient in need thereof.

17 Claims, 12 Drawing Sheets

(56) References Cited

OTHER PUBLICATIONS

Bergen et al.; "Colistin Methanesulfonate Is an Inactive Prodrug of Colistin Against Pseudomonas Aeruginosa"; Antimicrobial Agents and Chemotherapy; pp. 1953-1958; (2006).
Bossche et al.; "Identification of Impurities in Polymyxin B and Colistin Bulk Sample Using Liquid Chromatography Coupled to Mass Spectrometry"; Talanta; 82; pp. 1521-1529; (2011).
European Medicines Agency: "Review Under Article 5(3) of Regulation EC(No) 726-2004; Polymyxin-based products"; retrieved from the Internet: URL:http://www.ema.europa.eu/docs/en_GB/document_library/Report/2015/05/WC500187326.pdf. Retrieved on Sep. 7, 2015.
Govaerts et al.; "Mass Spectrometric Fragmentation of Cyclic Peptides Belonging to the Polymyxin and Colistin Antibiotics Studied by Ion Trap and Quadrupole/Orthogonal-Acceleration Time-of-Flight Technology"; Rapid Comm. in Mass Spectrometry; 16; (2002).
He et al.; "Pharmacokinetics of Four Different Brands of Colistimethate and Formed Colistin in Rats"; J Antimicrob Chemother; 68; pp. 2311-2317; (2013).
Healan et al.; "Stability of Colistimethate Sodium in Aqueous Solution"; AAC.ASM.Org; 56(12); pp. 6432-6433; (2012); downloaded Mar. 23, 2017 http://aac.asm.org.
Li et al.; "Evaluation of Colistin as an Agent Against Multi-resistant Gram-negative Bacteria"; International Journal of Antimicrobial Agents; 25(1); pp. 11-25; (2005).
Li et al.; "Stability of Colistin and Colistin Methanesulfonate in Aqueous Media and Plasma as Determined by High Performance Liquid Chromatography"; Antimicrobial Agents and Chemotherapy; 47(4); pp. 1364-1370; (2003).
Magee et al.; "Discovery of Dap-3 Polymyxin Analogues for the Treatment of Multidrug-Resistant Gram-Negative Nosocomial Infections"; Journal of Medicinal Chemistry; 53(12); pp. 5079-5093; (2013).
McMillian et al.; "Sodium Colistimethate I: Dissociations of Aminomethanesulfonates in Aqueous Solution"; Journal of Pharmaceutical Sciences; ; 58(6); pp. 730-737; (1969).
Shorin et al. "Antibacterial Activity, Toxicity and Medicinal Properties of Monomycin and Colimycin Methanesulfonates" Database CA [on-line]Chemical Abstracts Service, Columbus, Ohio, Database accession No. 56:38870; 4 pages (1961).
Wishart et al.; "1H, 13C and 15N Chemical Shift Referencing in Biomolecular NMR"; Journal of Biomolecular NMR; 6; pp. 135-140; (1995).
Storm et al.; "Polymyxin and Related Peptide Antibiotics"; Annual Review of Biochemistry; 46; pp. 723-763; (1977).
Van den Bossche et al.; "Identification of Impurities in Polymyxin B and Colistin Bulk Sample Using LiquidChromatography Coupled to Mass Spectrometry"; Talanta; 83; pp. 1521-1529; (2011).
Wallace et al.; "Self-assembly Behaviour of Colistin and its Prodrug Colistin Methanesulfonate: Implications for Solution Stability and Solubilization"; J. Phys Chem B., Author Manuscript: 114(14); pp. 4836-4840; (2010).
Wallace et al.; "Stability of Colistin Methanesulfonate in Pharmaceutical Products and Solutions for Administration to Patients"; Antimicrobial Agents and Chemotherapy; pp. 3047-3051; (2008).
European Medicines Agency Assessment report of polymixin-based products, EMA/CHMP/153652/2015, dated Feb. 26, 2015.
Suter et al.; "The Sulfomethylation Reaction"; J. Org. Chem.; 10(5); pp. 470-478; (1945).
Falagas et al.; "Use of International Units When Dosing Colistin Will Help Decrease Confusion Related to Various Formulations of the Drug Around the World"; Antimicrobial Agents and Chemotherapy; pp. 2274-2275; (2006).
Barnett et al.; "Sodium Sulphomethyl Derivatives of Polymyxins"; Birt. J. Pharmacol, 23, pp. 552-574; (1964).
Coly-Mycin M Parenteral (Colistimethate for Injection, USP), Prescribing Information as of Feb. 2011; JHP Pharmaceuticals Ref: 300818F, 5 pages.
Final Office Action, dated Oct. 26, 2018; U.S. Appl. No. 15/516,243, filed Mar. 31, 2017, 15 pages.
NonFinal Office Action, dated May 23, 2018, U.S. Appl. No. 15/516,243, filed Mar. 31, 2017; 42 pages.
Particles in Injections; printed Mar. 26, 2019; 4 pages; http://www.uspbpep.com/usp32/pub/data/v32270/usp32n127s0_c1.html.
Tawde, Suprita A.; "Particulate Matter in Injectables: Main Cause for Recalls"; J. Pharmacovigil; 3(1); e128; 3 pages; (2014).
Tobramycin Inhalation Soluation; printed Mar. 22, 2019; 4 pages; http://www.uspbpep.com/usp32/pub/data/v32270/usp32nf27s)_m83766.html; 4 pages.
Colomycin: Package Leaflet: Information for the User; Power for Solution for Injection, Infusion or Inhalation Colistimethate Sodium; TEVA UK Limited; Manufacturer and site of batch release: Millmount Healthcare Ltd; Leaflet issued Jul. 2019; 2 pages.
Ratjen et al.; "Pharmacokinetics of Inhaled Colistin in Patients with Cystic Fibrosis"; Journal of AntimicrobialChemotherapy; 57(2); pp. 306-311; (2006).
UW Health: Nebulized Colistimethate (Coly-Mycin) or Colistin, produced by the Department of Nursing HF#5851, Aug. 2019.
Liu, W. et al.; "Biopharmaceutical Manufacturing Using Blow-Fill-Seal Technology"; BioPharm International, vol. 24, Issue No. 7; 2011; pp. 22-29.

\* cited by examiner

Fig. 3

INHALATION DEVICE

CROSS REFERENCE TO RELATED APPLICATIONS

This application is a National Stage application of PCT/EP2015/072736, filed on Oct. 1, 2015, which claims the benefit of U.S. Provisional Application No. 62/059,748, filed on Oct. 3, 2014, both of which are incorporated by reference in their entirety herein.

FIELD OF THE INVENTION

Disclosed herein is a pulmonary administration device, comprising a spray nozzle unit and a cartridge containing an aqueous solution comprising from 70 to 400 mg A/mL of a sulfomethylated polymyxin, and its use in therapy for pulmonary administration in a patient in need thereof.

BACKGROUND

Bacterial lung infection is a major problem and may become life threatening for patients suffering from chronic lung disorders, such as asthma, cystic fibrosis (CF), non CF bronchiectasis and chronic obstructive pulmonary disease.

Colistin is a multicomponent polymyxin antibiotic produced by *Bacillus polymyxa* var. *colistinus* that is useful for the treatment of serious bacterial lung infections caused by gram negative bacteria, such as, for example, *Pseudomonas Aeruginosa* or *Klebsiella pneumoniae*. Polymyxin E1 and Polymyxin E2 are the major components of colistin.

When colistin is sulfomethylated, Colistimethate sodium (CMS) can be obtained. In order to become an effective antimicrobial agent, the sulfomethyl groups of CMS need to be hydrolysed thereby liberating free amino-groups. Thus, CMS is considered to be a pro-drug of colistin. The accepted consensus is that in aqueous solutions, CMS spontaneously hydrolyses and forms a complex mixture of sulfomethylated colistin derivatives and possibly colistin. It is widely accepted that a CMS drug product should not contain an amount of colistin considered to be efficacious in vivo because administration of colistin results in noted toxicities.

Coly-Mycin® M Parenteral is a drug containing CMS approved for injection. The label instructs that "parenteral drug products should be inspected visually for particulate matter and discoloration prior to administration, whenever solution and container permit. If these conditions are observed, the product should not be used. [ . . . ] Any final intravenous infusion solution containing colistimethate sodium should be freshly prepared and used for no longer than 24 hours."

Promixin is a drug containing CMS approved for inhalation. The label instructs that "solutions should be used immediately after reconstitution (see section 4.2). Any unused solution remaining in the nebulizer must be discarded following treatment."

A FDA alert published in 2007 following the death of a CF patient linked to the inhalation of an aged CMS solution states that "Premixing colistimethate into an aqueous solution and storing it for longer than 24 hours results in increased concentrations of colistin in solution, increasing the potential for lung toxicity. [ . . . ] In aqueous solution, colistimethate undergoes spontaneous hydrolysis to form colistin."

It has now been discovered that an aqueous solution comprising high concentration of a sulfomethylated polymyxin exhibits physicochemical properties suitable for long-term stability, even at room temperature. Thus it may be utilized in a pulmonary administration device, which may be utilized in the aforementioned therapeutic applications in humans.

SUMMARY

Disclosed herein is a pulmonary administration device, comprising a spray nozzle unit and a cartridge containing an aqueous solution comprising from 70 to 400 mg A/mL of a sulfomethylated polymyxin, and its use in therapeutic or prophylactic treatment of bacterial infections in the pulmonary system by pulmonary administration.

DETAILED DESCRIPTION

Brief Description of the Figures

FIG. 3. Scatterplot of cumulative mass (%) vs. aerodynamic diameter for Example 4 composition.

DEFINITIONS

Figure 1:
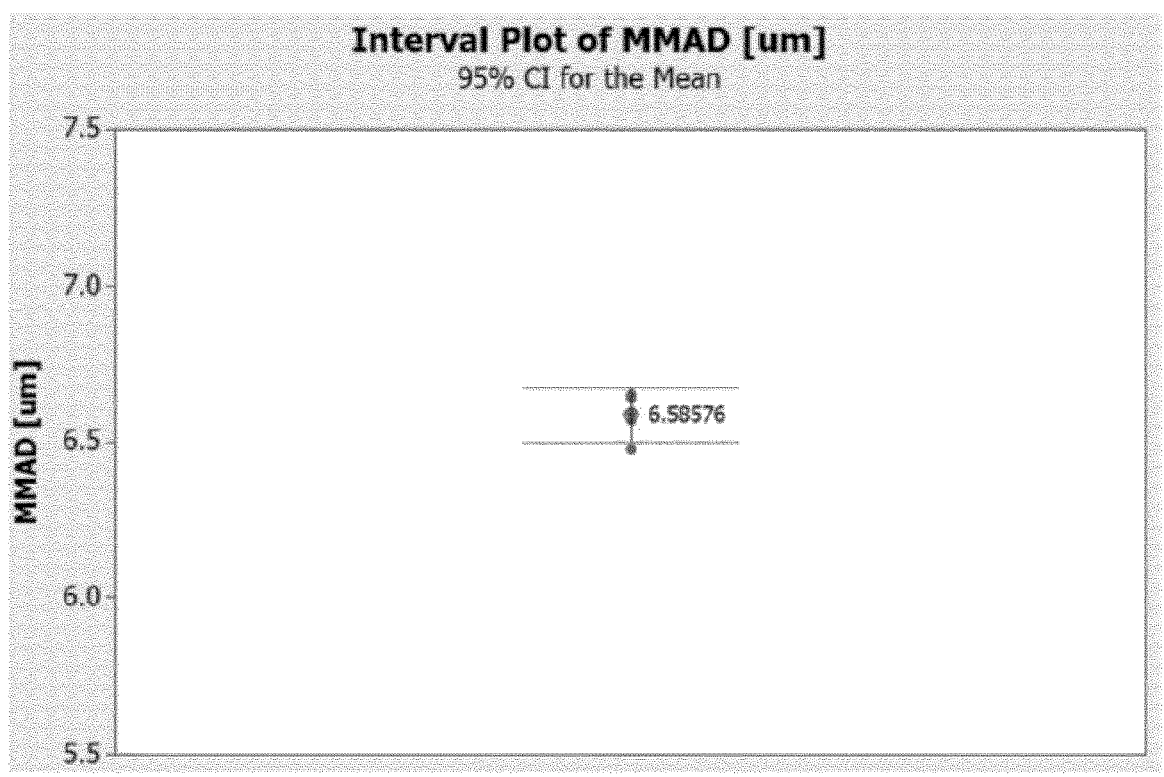
FIG. 1. Interval plot of mass median aerodynamic diameter (μm) of the Example 4 composition.

The phrase "a" or "an" entity as used herein refers to one or more of that entity; for example, a compound refers to one or more compounds or at least one compound.

As such, the terms "a" (or "an"), "one or more", and "at least one" can be used interchangeably herein.

Numerals used herein referring to a physicochemical property, time, temperature, concentration, particle size, and the like, are understood to represent measured values, and, as such, should not be strictly construed as being absolute, but rather be construed so as to account for experimental error and rounding. For example, a temperature value of 2° C. will be understood to have a certain degree of variance based on the instrument used to measure the temperature, e.g., glass thermometer, digital thermometer, etc. Moreover, a measured temperature of 1.6° C., when rounded up, would be equivalent to a temperature value of 2° C.

The term "chromatographic profile," as used herein, means an HPLC chromatogram obtained by a method capable of separating or display at least 50 peaks present in CMS. Such method can be found in WO 2014/195405.

The term "no significant change in the chromatographic profile" is meant to include chromatograms in which the relative peak intensity is relatively stable, for example, varies less than 5%, or more preferably, less than 2%.

The term "physicochemical property," as used herein, means a parameter that is a measure of a physicochemical property, such as, for example, sub-visible particles, number of visible particles, color, clarity, pH, osmolality, turbidity, or viscosity.

The approximate relationship between colistin base activity per volume, and the resultant antibacterial activity of the solution as measured in International Units per mL (IU/mL) is shown in Table 1 below. The activity of CMS depends on the potency measured and the water content.

TABLE 1

| Colistin base activity per ml (mg A/ml) | Million International units per ml (MIU/ml) |
|---|---|
| 0.4 | 0.0125 |
| 37.5 | 1.125 |
| 75 | 2.25 |
| 112.5 | 3.375 |
| 150 | 4.5 |

The term "colistin base activity" is alternatively referred to herein as "A".

According to the FDA-approved Coly-Mycin M label from January 2013, colistimethate sodium is supplied in vials containing 150 mg colistin base activity. The vials should be reconstituted with 2 mL sterile water for injection to provide colistimethate sodium at a concentration equivalent to 75 mg/mL colistin base activity. In the present disclosure, we consider such solutions to contain 75 mg A/mL of CMS. Dissolving 3.0 MIU of CMS in 1.0 ml water will provide 100 mg A/mL of CMS. Dissolving 2.8 MIU of CMS in 1.0 ml water will provide 94 mg A/mL of CMS.

The term "aqueous solution" as used herein, means a solution in which water is the principle (or majority) solvent. Suitable aqueous solutions for sulfomethylated polymyxins include, but are not limited to water for injection (WFI), ultrapure water, 0.9% saline solution and 0.45% saline solution.

The term "CMS" as described herein refers to a composition comprising sulfomethylated polymyxin E1 and sulfomethylated polymyxin E2. The Chemical Abstracts Registry (CAS) has assigned such a composition the number 8068-28-8 for CMS. In general, CMS is considered to be the mixture of sulfomethylated colistin.

The term "colistin" as described herein refers to a composition comprising polymyxin E1 and polymyxin E2. Chemical abstracts have assigned the number 1066-17-7 for colistin. According to the European Pharmacopoeia, colistin should comprise more than 77% of Polymyxin E1, E2, E3, E1i and E1-7MOA, but less than 10% of each of the minor components Polymyxin E3, E1-i and E1-MOA. The term "Polymyxin E" as described herein is used interchangeably with "colistin".

The term "Polymyxin E1" as described herein refers to the compound having the CAS no 7722-44-3. Polymyxin E1 is used interchangeably with colistin A.

The term "Polymyxin E2" as described herein refers to the compound having the CAS no 7239-48-7. Polymyxin E2 is used interchangeably with colistin B.

The term "Polymyxin B" as used herein, refers to the compound having the CAS no. 1405-20-5.

The term "sulfomethylated polymyxin" as used herein refers to a polymyxin comprising at least one sulfomethyl ($-CH_2S(O)_2OR^3$) group attached to a γ-amino group on an L-DAB (or L-DBU) residue, which the $R^3$ radical can be H or M, where M is a monovalent cation, which refers to a cationic species containing a single positive charge, examples of which include, but are not limited to $Li^+$, $Na^+$, $K^+$, $H_mN(C_{1-4} alkyl)_n^+$, where m is 0-4 and n is 0-4 with the proviso that m+n=4.

The term "DAB" as described herein, refers the radical derived from 2,4-diaminobutanoic acid, in which the carbon atom adjacent to the carbonyl carbon (i.e., the α-carbon) has a stereochemistry designated as the L-configuration. L-DAB is alternatively referred to in the literature as L-DBU.

The most common sulfomethylated polymyxin is called CMS, but other sulfomethylated polymyxins exist, for example, sulfomethylated Polymyxin B, sulfomethylated Polymyxin E1, sulfomethylated Polymyxin E2 etc. Sulfomethylated polymyxins are also disclosed in PCT published application WO 2014/108469 (Xellia), the subject matter of which is incorporated by reference in its entirety. Additional polymyxins are described in PCT published application WO 2012/168820, which corresponds to US 2012/0316105, the subject matter of which is incorporated by reference in its entirety.

The term "cartridge," as used herein means a vessel suitable for storage of aqueous solutions comprising sulfomethylated polymyxins.

The term "mOsm/kg," as related to osmolality, as used herein means milliosmole per kg.

The term "NTU," as related to turbidity, as used herein means Nephelometric Turbidity Units.

The term "USP <No.>," as used herein refers to a specifically numbered monograph, as described in The United States Pharmacopeia (USP 35, May 1, 2012).

The term "Ph. Eur.," followed by a designated numeric code, as used herein, refers to the European Pharmacopoeia, Eight Edition, Volume 1, 2013.

The term "nominal volume," as used herein refers to the volume specified by a cartridge manufacturer.

"pH" is the conventional measurement unit for hydrogen ion activity in a solution at 25° C. unless other temperature is specified. The suitable pH range for the aqueous CMS solutions in the cartridges according to the present invention is 6-9, such as 6.5-8.5. The most preferred pH range for the aqueous CMS solutions in the cartridges according to the present invention is 6.0-7.0.

A first embodiment is directed to a pulmonary administration device, comprising a spray nozzle unit and a cartridge containing an aqueous solution comprising from 70 to 400 mg A/mL of a sulfomethylated polymyxin.

In a first aspect of the first embodiment, the concentration of the sulfomethylated polymyxin ranges from 80 to 150 mg A/mL.

In a second aspect of the first embodiment, the concentration of the sulfomethylated polymyxin ranges from 85 to 150 mg A/mL.

In a third aspect of the first embodiment, the concentration of the sulfomethylated polymyxin ranges from 90 to 150 mg A/mL.

In a fourth aspect of the first embodiment, the concentration of the sulfomethylated polymyxin ranges from 100 to 120 mg A/mL.

In a fifth aspect of the first embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a sixth aspect of the first embodiment, the aqueous solution contains an acceptable amount of foreign matter as determined by USP <1>.

In a seventh aspect of the first embodiment, the aqueous solution is free of visible particles, as determined by USP <1>.

In an eighth aspect of the first embodiment, the aqueous solution has an acceptable clarity, as determined by USP <1>.

In a ninth aspect of the first embodiment, the aqueous solution has a turbidity of not more than 3 NTU, as determined by Ph. Eur. 2.2.1.

In a 10th aspect of the first embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the first embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the first embodiment, the aqueous solution has a pH from 6 to 8.

In a 13th aspect of the first embodiment, the cartridge has a nominal volume of 1.0 or 0.5 mL.

In a 14th aspect of the first embodiment, the aqueous solution has an osmolality from 500 mOsm/kg to 1300 mOsm/kg.

In a 15th aspect of the first embodiment, the aqueous solution has an osmolality from 700 mOsm/kg to 1200 mOsm/kg.

In a 16th aspect of the first embodiment, the aqueous solution has an osmolality from 900 mOsm/kg to 1200 mOsm/kg.

In a 17th aspect of the first embodiment, the device further comprises a pressurized container.

A second embodiment is directed to a pulmonary administration device, comprising a spray nozzle unit and a cartridge containing an aqueous solution comprising from 70 to 400 mg A/mL of colistimethate sodium In a first aspect of the second embodiment, the concentration of the colistimethate sodium ranges from 80 to 200 mg A/mL.

In a second aspect of the second embodiment, the concentration of the colistimethate sodium ranges from 80 to 120 mg A/mL.

In a third aspect of the second embodiment, the concentration of the colistimethate sodium ranges from 85 to 113 mg A/mL.

In a fourth aspect of the second embodiment, the concentration of the colistimethate sodium ranges from 100 to 120 mg A/mL.

In a fifth aspect of the second embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a sixth aspect of the second embodiment, the aqueous solution contains an acceptable amount of foreign matter as determined by USP <1>.

In a seventh aspect of the second embodiment, the aqueous solution is free of visible particles, as determined by USP <1>.

In an eighth aspect of the second embodiment, the aqueous solution has an acceptable clarity, as determined by USP <1>.

In a ninth aspect of the second embodiment, the aqueous solution has a turbidity of not more than 3 NTU, as determined by Ph. Eur. 2.2.1.

In a 10th aspect of the second embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the second embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the second embodiment, the aqueous solution has a pH from 6 to 8.

In a 13th aspect of the second embodiment, the cartridge has a nominal volume of 1.0 or 0.5 mL.

In a 14th aspect of the second embodiment, the aqueous solution has an osmolality from 500 mOsm/kg to 1300 mOsm/kg.

In a 15th aspect of the second embodiment, the aqueous solution has an osmolality from 700 mOsm/kg to 1200 mOsm/kg.

In a 16th aspect of the second embodiment, the aqueous solution has an osmolality from 900 mOsm/kg to 1200 mOsm/kg.

In a 17th aspect of the second embodiment, the device further comprises a pressurized container.

An aqueous Metered-Dose Inhaler (aMDI) is a device that delivers a specific amount of medication to the lungs, in the form of a short burst of droplets of medicine that is inhaled by the patient.

Metered dose inhalers (MDI) suitable according to the embodiments disclosed herein, is coordinated with actuation of the inhaler. Thus the administration comprises one inhalation for each actuation of the device. The actuation of the device can be triggered by various means known in the field, for example, manually or by “breath sensors”. When a metered dose inhaler is actuated by the use of breath sensors and thus by inhalation only, the composition is administered by “breath actuated inhalation”.

When a metered dose inhaler is actuated manually at the same time as the patients performs one inhalation, the composition is administered by “coordinated inhalation”.

Typical administration time for one inhalation with an aMDI is a few seconds. This maneuver can be repeated several times to obtain the desired dose. The most preferred aMDIs for use in the present invention produce monodisperse particles with a mass median aerodynamic diameter (MMAD) of from 4 to 8 µm, or on average 6 µm.

An aMDI suitable for the administration of a composition according to the present invention is capable of forming distinct and uniform aerosol droplets of a mean diameter between 4 to 8 micron of an aqueous solution comprising sulfomethylated polymyxins. PCT published application WO 95/13860 (which corresponds to U.S. Pat. No. 5,753,014, incorporated by reference) describes membrane filters provided with pores having a pore size of typically between 5 nm and 50 µm. Membranes disclosed therein having pores of a size providing aerosols having a mass median aerodynamic diameter of 4-8 µm may preferably be used in a spray nozzle unit placed in a metered dose inhaler, such as e.g. a metered dose inhaler disclosed in WO 2011/043712 (which corresponds to US 2012/0216805, incorporated by reference), to administer a highly concentrated CMS composition according to the present invention.

A third embodiment is directed to an aqueous composition and/or an aqueous solution comprising from 70 to 400 mg A/mL of a sulfomethylated polymyxin for use in therapeutic or prophylactic treatment of bacterial infection in the pulmonary system, wherein the solution is for pulmonary administration.

By aerosolization of the aqueous composition of the first embodiment or second embodiment, a method for pulmonary administration has also been provided.

Every embodiments and aspects concerning the method for pulmonary administration of the present invention is likewise applicable for the composition and/or aqueous solution for medical use according to the third embodiment.

A fourth embodiment is directed to a method for pulmonary administration in a patient in need thereof, which comprises: actuating an inhaler comprising a spray nozzle unit and a cartridge containing an aqueous solution comprising from 70 to 400 mg A/mL of a sulfomethylated polymyxin; and administering the aqueous solution to the patient in the form of droplets having a mass median aerodynamic diameter of from 4 to 8 µm.

In a first aspect of the third and fourth embodiment, the concentration of the sulfomethylated polymyxin ranges from 80 to 200 mg A/mL.

In a second aspect of the third and fourth embodiment, the concentration of the sulfomethylated polymyxin ranges from 80 to 120 mg A/mL.

In a third aspect of the third and fourth embodiment, the concentration of the sulfomethylated polymyxin ranges from 85 to 113 mg A/mL.

In a fourth aspect of the third and fourth embodiment, the concentration of the sulfomethylated polymyxin ranges from 100 to 120 mg A/mL.

In a fifth aspect of the third and fourth embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL.

In a sixth aspect of the third and fourth embodiment, the aqueous solution contains an acceptable amount of foreign matter as determined by USP <1>.

In a seventh aspect of the third and fourth embodiment, the aqueous solution is free of visible particles, as determined by USP <1>.

In an eighth aspect of the third and fourth embodiment, the aqueous solution has an acceptable clarity, as determined by USP <1>.

In a ninth aspect of the third and fourth embodiment, the aqueous solution has a turbidity of not more than 3 NTU, as determined by Ph. Eur. 2.2.1.

In a 10th aspect of the third and fourth embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the third and fourth embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the third and fourth embodiment, the aqueous solution has a pH from 6 to 8.

In a 13th aspect of the third and fourth embodiment, the cartridge has a nominal volume of 1.0 or 0.5 mL.

In a 14th aspect of the third and fourth embodiment, the aqueous solution has an osmolality from 500 mOsm/kg to 1300 mOsm/kg.

In a 15th aspect of the third and fourth embodiment, the aqueous solution has an osmolality from 700 mOsm/kg to 1200 mOsm/kg.

In a 16th aspect of the third and fourth embodiment, the aqueous solution has an osmolality from 900 mOsm/kg to 1200 mOsm/kg.

In a 17th aspect of the third and fourth embodiment, the sulfomethylated polymyxin is colistimethate sodium.

In an 18th aspect of the third and fourth embodiment, the spray nozzle unit provides droplets by Rayleigh breakup.

In an 19th aspect of the third and fourth embodiment, the spray nozzle unit has orifices with a diameter of from 1.5 to 2.2 µm.

Every embodiments and aspects concerning the method for pulmonary administration in a specific patient is likewise defined as a patient group in the embodiments and aspects related to the composition and/or aqueous solution for medical use.

In a 20th aspect of the third and fourth embodiment, the patient is infected with a gram negative bacteria.

In a 21st aspect of the third and fourth embodiment, the patient is infected with a gram negative bacteria and the gram negative bacteria is *Enterobacter aerogenes, Escherichia coli, Klebsiella pneumonaiae, Pseudomonas aeruginosa*, or a combination thereof.

In a 22nd aspect of the third and fourth embodiment, the patient suffers from a chronic lung disorder and is infected with a gram negative bacteria and the gram negative bacteria is *Enterobacter aerogenes, Escherichia coli, Klebsiella pneumonaiae, Pseudomonas aeruginosa*, or a combination thereof.

In a 23rd aspect of the third and fourth embodiment, the patient suffers from a chronic lung disorder selected from among, asthma, cystic fibrosis (CF), non-CF bronchiectasis, a chronic obstructive pulmonary disease, or a combination thereof, and the patient is infected with a gram negative bacteria and the gram negative bacteria is *Enterobacter aerogenes, Escherichia coli, Klebsiella pneumonaiae, Pseudomonas aeruginosa*, or a combination thereof.

In a 24th aspect of the third and fourth embodiment, the device further comprises a pressurized container.

A fifth embodiment is directed to a method for pulmonary administration in a patient in need thereof, which comprises: actuating an inhaler comprising a spray nozzle unit and a cartridge containing an aqueous solution comprising from 70 to 400 mg A/mL of colistimethate sodium; and administering the aqueous solution to the patient in the form of droplets having a mass median aerodynamic diameter of from 4 to 8 μm.

In a first aspect of the fifth embodiment, the concentration of the colistimethate sodium ranges from 80 to 200 mg A/mL.

In a second aspect of the fifth embodiment, the concentration of the colistimethate sodium ranges from 80 to 120 mg A/mL.

In a third aspect of the fifth embodiment, the concentration of the colistimethate sodium ranges from 85 to 113 mg A/mL.

In a fourth aspect of the fifth embodiment, the concentration of the colistimethate sodium ranges from 100 to 120 mg A/mL.

In a fifth aspect of the fifth embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a sixth aspect of the fifth embodiment, the aqueous solution contains an acceptable amount of foreign matter as determined by USP <1>.

In a seventh aspect of the fifth embodiment, the aqueous solution is free of visible particles, as determined by USP <1>.

In an eighth aspect of the fifth embodiment, the aqueous solution has an acceptable clarity, as determined by USP <1>.

In a ninth aspect of the fifth embodiment, the aqueous solution has a turbidity of not more than 3 NTU, as determined by Ph. Eur. 2.2.1.

In a 10th aspect of the fifth embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the fifth embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the fifth embodiment, the aqueous solution has a pH from 6 to 8.

In a 13th aspect of the fifth embodiment, the cartridge has a nominal volume of 1.0 or 0.5 mL.

In a 14th aspect of the fifth embodiment, the aqueous solution has an osmolality from 500 mOsm/kg to 1300 mOsm/kg.

In a 15th aspect of the fifth embodiment, the aqueous solution has an osmolality from 700 mOsm/kg to 1200 mOsm/kg.

In a 16th aspect of the fifth embodiment, the aqueous solution has an osmolality from 900 mOsm/kg to 1200 mOsm/kg.

In a 17th aspect of the fifth embodiment, the spray nozzle unit provides droplets by Rayleigh breakup.

In a 18th aspect of the fifth embodiment, the spray nozzle unit has orifices with a diameter of from 1.5 to 2.2 μm.

In a 19th aspect of the fifth embodiment, the patient is infected with a gram negative bacteria.

In a 20th aspect of the fifth embodiment, the patient is infected with a gram negative bacteria and the gram negative bacteria is *Enterobacter aerogenes, Escherichia coli, Klebsiella pneumonaiae, Pseudomonas aeruginosa*, or a combination thereof.

In a 21st aspect of the fifth embodiment, the patient suffers from a chronic lung disorder and is infected with a gram negative bacteria and the gram negative bacteria is *Enterobacter aerogenes, Escherichia coli, Klebsiella pneumonaiae, Pseudomonas aeruginosa*, or a combination thereof.

In a 22nd aspect of the fifth embodiment, the patient suffers from a chronic lung disorder selected from among, asthma, cystic fibrosis (CF), non-CF bronchiectasis, a chronic obstructive pulmonary disease, or a combination thereof, and the patient is infected with a gram negative bacteria and the gram negative bacteria is *Enterobacter aerogenes, Escherichia coli, Klebsiella pneumonaiae, Pseudomonas aeruginosa*, or a combination thereof.

In a 23rd aspect of the fifth embodiment, the device further comprises a pressurized container.

A sixth embodiment is directed to a method for pulmonary administration in a patient in need thereof, which comprises: actuating an inhaler comprising a spray nozzle unit and a cartridge containing an aqueous solution comprising from 70 to 400 mg A/mL of a sulfomethylated polymyxin; and administering the aqueous solution to the patient in the form of droplets having a mass median aerodynamic diameter of from 5.5 to 7.5 μm.

In a first aspect of the sixth embodiment, the concentration of the sulfomethylated polymyxin ranges from 80 to 150 mg A/mL.

In a second aspect of the sixth embodiment, the concentration of the sulfomethylated polymyxin ranges from 85 to 150 mg A/mL.

In a third aspect of the sixth embodiment, the concentration of the sulfomethylated polymyxin ranges from 90 to 150 mg A/mL.

In a fourth aspect of the sixth embodiment, the concentration of the sulfomethylated polymyxin ranges from 100 to 120 mg A/mL.

In a fifth aspect of the sixth embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a sixth aspect of the sixth embodiment, the aqueous solution contains an acceptable amount of foreign matter as determined by USP <1>.

In a seventh aspect of the sixth embodiment, the aqueous solution is free of visible particles, as determined by USP <1>.

In an eighth aspect of the sixth embodiment, the aqueous solution has an acceptable clarity, as determined by USP <1>.

In a ninth aspect of the sixth embodiment, the aqueous solution has a turbidity of not more than 3 NTU, as determined by Ph. Eur. 2.2.1.

In a 10th aspect of the sixth embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the sixth embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the sixth embodiment, the aqueous solution has a pH from 6 to 8.

In a 13th aspect of the sixth embodiment, the cartridge has a nominal volume of 1.0 or 0.5 mL.

In a 14th aspect of the sixth embodiment, the aqueous solution has an osmolality from 500 mOsm/kg to 1300 mOsm/kg.

In a 15th aspect of the sixth embodiment, the aqueous solution has an osmolality from 700 mOsm/kg to 1200 mOsm/kg.

In a 16th aspect of the sixth embodiment, the aqueous solution has an osmolality from 900 mOsm/kg to 1200 mOsm/kg.

In a 17th aspect of the sixth embodiment, the sulfomethylated polymyxin is colistimethate sodium.

In an 18th aspect of the sixth embodiment, the spray nozzle unit provides droplets by Rayleigh breakup.

In a 19th aspect of the sixth embodiment, the spray nozzle unit has an orifice with a diameter of from 1.5 to 2.2 μm.

In a 20th aspect of the sixth embodiment, the patient is infected with a gram negative bacteria.

In a 21st aspect of the sixth embodiment, the patient is infected with a gram negative bacteria and the gram negative bacteria is *Enterobacter aerogenes, Escherichia coli, Klebsiella pneumonaiae, Pseudomonas aeruginosa*, or a combination thereof.

In a 22nd aspect of the sixth embodiment, the patient suffers from a chronic lung disorder and is infected with a gram negative bacteria and the gram negative bacteria is *Enterobacter aerogenes, Escherichia coli, Klebsiella pneumonaiae, Pseudomonas aeruginosa*, or a combination thereof.

In a 23rd aspect of the sixth embodiment, the patient suffers from a chronic lung disorder selected from among, asthma, cystic fibrosis (CF), non-CF bronchiectasis, a chronic obstructive pulmonary disease, or a combination thereof, and the patient is infected with a gram negative bacteria and the gram negative bacteria is *Enterobacter aerogenes, Escherichia coli, Klebsiella pneumonaiae, Pseudomonas aeruginosa*, or a combination thereof.

In a 24th aspect of the sixth embodiment, the device further comprises a pressurized container.

A seventh embodiment is directed to a method for pulmonary administration in a patient in need thereof, which comprises: actuating an inhaler comprising a spray nozzle unit and a cartridge containing an aqueous solution comprising from 70 to 400 mg A/mL of colistimethate sodium; and administering the aqueous to the patient in the form of droplets having a mass median aerodynamic diameter of from 5.5 to 7.5 μm.

In a first aspect of the seventh embodiment, the concentration of the colistimethate sodium ranges from 80 to 200 mg A/mL.

In a second aspect of the seventh embodiment, the concentration of the colistimethate sodium ranges from 80 to 120 mg A/mL.

In a third aspect of the seventh embodiment, the concentration of the colistimethate sodium ranges from 85 to 113 mg A/mL.

In a fourth aspect of the seventh embodiment, the concentration of the colistimethate sodium ranges from 100 to 120 mg A/mL.

In a fifth aspect of the seventh embodiment, the aqueous solution comprises from 90 to 120 mg A/mL of colistimethate sodium, and all concentrations included in said range, such as, 90 mg A/mL, 94 mg A/mL, 95 mg A/mL, 100 mg A/mL, 110 mg A/mL, 112.5 mg A/mL, 115 mg A/mL and 120 mg A/mL.

In a sixth aspect of the seventh embodiment, the aqueous solution contains an acceptable amount of foreign matter as determined by USP <1>.

In a seventh aspect of the seventh embodiment, the aqueous solution is free of visible particles, as determined by USP <1>.

In an eighth aspect of the seventh embodiment, the aqueous solution has an acceptable clarity, as determined by USP <1>.

In a ninth aspect of the seventh embodiment, the aqueous solution has a turbidity of not more than 3 NTU, as determined by Ph. Eur. 2.2.1.

In a 10th aspect of the seventh embodiment, the aqueous solution has an acceptable amount of foreign matter, as determined by USP <1>; has an acceptable clarity, as determined by USP <1>; and has a turbidity of not more than 3 NTU, as determined by Ph. Eur. 2.2.1.

In an 11th aspect of the seventh embodiment, the aqueous solution is free of visible particles, as determined by USP <1>, has an acceptable clarity, as determined by USP <1>; and has a turbidity of not more than 3 NTU, as determined by Ph. Eur. 2.2.1.

In a 12th aspect of the seventh embodiment, the aqueous solution has a pH from 6 to 8.

In a 13th aspect of the seventh embodiment, the cartridge has a nominal volume of 1.0 or 0.5 mL.

In a 14th aspect of the seventh embodiment, the aqueous solution has an osmolality from 500 mOsm/kg to 1300 mOsm/kg.

In a 15th aspect of the seventh embodiment, the aqueous solution has an osmolality from 700 mOsm/kg to 1200 mOsm/kg.

In a 16th aspect of the seventh embodiment, the aqueous solution has an osmolality from 900 mOsm/kg to 1200 mOsm/kg.

In a 17th aspect of the seventh embodiment, the spray nozzle unit provides droplets by Rayleigh breakup.

In an 18th aspect of the seventh embodiment, the spray nozzle unit has orifices with a diameter of from 1.5 to 2.2 μm.

In a 19th aspect of the seventh embodiment, the patient is infected with a gram negative bacteria.

In a 20th aspect of the seventh embodiment, the patient is infected with a gram negative bacteria and the gram negative bacteria is *Enterobacter aerogenes, Escherichia coli, Klebsiella pneumonaiae, Pseudomonas aeruginosa*, or a combination thereof.

In a 21st aspect of the seventh embodiment, the patient suffers from a chronic lung disorder and is infected with a gram negative bacteria and the gram negative bacteria is *Enterobacter aerogenes, Escherichia coli, Klebsiella pneumonaiae, Pseudomonas aeruginosa*, or a combination thereof.

In a 22nd aspect of the seventh embodiment, the patient suffers from a chronic lung disorder selected from among, asthma, cystic fibrosis (CF), non-CF bronchiectasis, a chronic obstructive pulmonary disease, or a combination thereof, and the patient is infected with a gram negative bacteria and the gram negative bacteria is *Enterobacter aerogenes, Escherichia coli, Klebsiella pneumonaiae, Pseudomonas aeruginosa*, or a combination thereof.

In a 23rd aspect of the seventh embodiment, the device further comprises a pressurized container.

As related to the fourth, fifth, sixth and seventh embodiments, and at least one of the aspects of these embodiments, the actuating may be effected by (i) either by the use of breath sensors and thus by "breath actuated inhalation" or (ii) actuated manually at the same time as the patients performs one inhalation and thus by "coordinated inhalation".

A sieve may be introduced to alleviate or prevent clogging of the nozzle. For example, a 1 μm sieve would keep particles present in the either the aqueous sulfomethylated polymyxin solution or the colistimethate sodium solution from reducing the performance of the inhalator over time. Reduced temperature also may reduce clogging during use. If the device according to the first or second embodiment is stored between the doses administered e.g. between a morning dose and an evening dose, the storage temperature would preferably be lower than 20° C. With respect to clogging problems, a storage temperature at 2-8° C. may be more preferred.

A separate technical solution to the problem with the degradation of CMS in aqueous solution is directed to a pulmonary administration device, comprising a spray nozzle unit and a two-chamber cartridge containing colistimethate sodium powder and an aqueous diluent which, upon mixing, provides an aqueous solution comprising from 20 to 75 mg A/mL of colistimethate sodium. Such two-chamber cartridges could be made as disclosed in U.S. Pat. No. 5,549,561 or US2011/0094188.

EXAMPLES

Not to be limited by way of example, the following examples serve to facilitate a better understanding of the subject matter disclosed herein.

Example 1

Three aqueous solutions comprising colistimethate sodium (CMS) at three different concentrations (37.5 mg A/mL, 75 mg A/mL, and 112.5 mg A/mL) were stored in airtight containers over a 1-week period of time.

The HPLC-chromatographic profile (data not shown) showed degradation in an aqueous composition comprising 37.5 mg A/mL CMS, but no significant degradation in an aqueous solution comprising either 75 mg A/mL CMS or 112.5 mg A/mL CMS.

Several parameters of the above-mentioned compositions were observed over the stated time period at temperatures (5° C. (data not shown), 25° C., 30° C., and 40° C.), which include, but are not limited to: appearance, foreign matter (USP <1>, the presence of visible particles ("VP") is non-compliant), clarity of solution (USP <1>, lack of clarity results in non-compliance), number of subvisible particles (both ≤10 μm and ≤25 μm, USP <788>), pH (USP <791>), osmolality (USP <785>), and turbidity (Ph. Eur. 2.2.1). The results of these observations are presented in Table 2.

TABLE 2

|  | 37.5 mg A/mL | | | 75 mg A/mL | | | 112.5 mg A/mL | | |
| --- | --- | --- | --- | --- | --- | --- | --- | --- | --- |
| Parameter | 25° C. | 30° C. | 40° C. | 25° C. | 30° C. | 40° C. | 25° C. | 30° C. | 40° C. |
| Appearance[a] | SYS[h] | SYS[h] | SYS[h] | SYS[h] | SYS[h] | SYS[h] | SYS[h] | SYS[h] | SYS[h] |
| Foreign Matter[b] | VP[i] | VP[i] | VP[i] | C[j] | VP[i] | VP[i] | C[j] | C[j] | C[j] |
| Clarity[c] | NC[k] | NC[k] | NC[k] | C[j] | NC[k] | NC[k] | C[j] | C[j] | C[j] |
| PN[d] ≤ 10 μm[e] | 217 | 185 | 275 | 469 | 129 | 176 | 93 | 74 | 144 |
| PN[d] ≤ 25 μm[f] | 4 | 6 | 3 | 14 | 1 | 6 | 5 | 2 | 4 |
| pH | 6.81 | 6.83 | 6.88 | 6.35 | 6.44 | 6.46 | 6.07 | 6.13 | 6.17 |
| Osmolality (Osm/kg) | 0.311 | 0.306 | 0.282 | 0.667 | 0.667 | 0.642 | 1.117 | 1.160 | 1.143 |
| Turbidity[g] | 3.60 | 6.26 | 1.32 | 1.96 | 0.68 | 0.50 | 0.50 | 0.64 | 1.03 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN),
[e]Not more than ("NMT") 3000/mL,
[f]NMT 300/mL,
[g]NMT 3NTU,
[h]Slightly yellow solution (SYS),
[i]Visible Particles (VP),
[j]Complies (C),
[k]Not clear (NC).

From this data, it can be seen that an aqueous solution having a concentration less than 80 mg A/mL CMS exhibited an unacceptable amount of foreign matter, clarity, and/or turbidity, and thus, may not be suitable for long-term storage as a ready-to-use composition, as related, to, for example, a parenteral, a nasal, and, an inhalation solution. This should be contrasted to an aqueous solution having a concentration greater than or equal to 80 mg A/mL CMS, which exhibited an acceptable amount of foreign matter, clarity, and turbidity. The stability studies were extended over a period of 3-months. The results of these studies (25° C.) are summarized in Table 3.

TABLE 3

| Parameter | 37.5 mg A/mL | | | 75 mg A/mL | | | 112.5 mg A/mL | | |
| --- | --- | --- | --- | --- | --- | --- | --- | --- | --- |
| | 1-wk | 1-mo | 3-mo | 1-wk | 1-mo | 3-mo | 1-wk | 1-mo | 3-mo |
| Appearance[a] | SYS[h] | SYS[h] | SYS[h] | SYS[h] | SYS[h] | SYS[h] | SYS[h] | SYS[h] | SYS[h] |
| Foreign Matter[b] | VP[i] | VP[i] | VP[i] | C[j] | VP[i] | VP[i] | C[j] | C[j] | C[j,l] |
| Clarity[c] | NC[k] | C[j] | NC[k] | C[j] | C[j] | NC[k] | C[j] | C[j] | C[j] |
| PN[d] ≤ 10 μm[e] | 217 | 50 | 54 | 469 | 50 | 68 | 93 | 23 | 55 |
| PN[d] ≤ 25 μm[f] | 4 | 5 | 2 | 14 | 3 | 1 | 5 | 2 | 2 |
| pH | 6.81 | 6.82 | 6.90 | 6.35 | 6.34 | 6.43 | 6.07 | 6.03 | 6.13 |
| Osmolality (Osm/kg) | 0.311 | 0.308 | 0.299 | 0.667 | 0.678 | 0.649 | 1.177 | 1.162 | 1.130 |
| Turbidity[g] | 3.60 | 3.69 | 1.42 | 1.96 | 1.97 | 0.38 | 0.50 | 0.46 | 0.46 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN) less than or equal to the stated value,
[e]Not more than ("NMT") 3000/mL,
[f]NMT 300/mL,
[g]NMT 3 NTU,
[h]Slightly yellow solution (SYS),
[i]Visible Particles (VP),
[j]Complies (C),
[k]Not clear (NC),
[l]3 of 5 vials showed no particles, with the 2 vials showed what appeared to be microbial growth.

The results in this table confirm that an aqueous solution having a concentration less than 75 mg A/mL CMS may not be suitable for long-term storage as a ready-to-use composition, but that an aqueous solution having a concentration greater than 80 mg A/mL CMS may be suitable for long-term storage as a ready-to-use composition, and thus, may be used in a cartridge suitable for parenteral, nasal, inhalation application.

As stated above, the package insert for the Coly-Mycin® M Parenteral drug product states that "[p]arenteral drug products should be inspected visually for particulate matter and discoloration prior to administration, whenever solution and container permit," and that "[i]f these conditions are observed, the product should not be used."

Accordingly, an unexpected and surprising result of the embodiments described herein is that the aqueous solution is free of visible particles, as determined by USP <1>, has an acceptable clarity, as determined by USP <1>; and has a turbidity of not more than 3 NTU, as determined by Ph. Eur. 2.2.1.

Example 2

Aqueous solutions comprising 94 mg A/mL colistimethate sodium (CMS) were stored in airtight containers for 1-month at different temperatures (5° C., 25° C., 30° C., and 40° C.). The HPLC-chromatographic profile (data not shown) showed no significant change. Several parameters of the above-mentioned composition were observed over the 1-month period of time, the results are summarized in Table 4.

TABLE 4

| Parameter | Initial | 5° C. | 25° C. | 30° C. | 40° C. |
| --- | --- | --- | --- | --- | --- |
| Appearance[a] | SYS[h] | SYS[h] | SYS[h] | SYS[h] | SYS[h] |
| Foreign Matter[b] | C[j] | C[j] | C[j] | C[j] | C[j] |
| Clarity[c] | C[j] | C[j] | C[j] | C[j] | C[j] |
| PN[d] ≤ 10 μm[e] | 102 | 11 | 34 | 33 | 59 |
| PN[d] ≤ 25 μm[f] | 2 | 0 | 2 | 3 | 1 |

TABLE 4-continued

| Parameter | Initial | 5° C. | 25° C. | 30° C. | 40° C. |
| --- | --- | --- | --- | --- | --- |
| pH | 6.21 | 5.98 | 6.09 | 6.11 | 6.13 |
| Osmolality (Osm/kg) | 0.928 | 0.916 | 0.925 | 0.908 | 0.929 |
| Turbidity[g] | 0.4 | 0.3 | 0.3 | 0.4 | 0.4 |

Specification and Notes Legend
[a]Colorless to slightly yellow solution,
[b]Free from visible particles,
[c]The solution is not significantly less clear than an equal volume of purified Water contained in a similar vessel and examined similarly.
[d]Number of sub-divisible particles (PN),
[e]Not more than ("NMT") 3000/mL,
[f]NMT 300/mL,
[g]NMT 3 NTU,
[h]Slightly yellow solution (SYS),
[i]Visible Particles (VP),
[j]Complies (C),
[k]Not clear (NC).

The results in this table confirm that a composition having a concentration greater than or equal to 80 mg A/mL CMS may be suitable for long-term storage as a ready-to-use composition. Observations for aqueous solutions comprising 112 mg A/ml colistimethate sodium (CMS) (data not shown) confirm that a composition having a concentration greater than 80 mg A/mL CMS may be suitable for long-term storage as a ready-to-use composition.

Example 3

Viscosity values for compositions comprising CMS at various concentrations were measured at 25° C. and the results are summarized in Table 5.

TABLE 5

| Sample | Conc. (mg A/ml) | Viscosity (cSt) |
| --- | --- | --- |
| Water | 0.0 | 0.94 |
| 1 | 37.5 | 1.25 |
| 2 | 75.0 | 1.89 |
| 3 | 94.0 | 2.24 |
| 4 | 112.5 | 3.05 |

The plotted viscosity (η) values versus concentration (c) values showed a quadratic relationship ($\eta=Ac^2+Bc+C$) with a good agreement ($R^2=0.9901$), in which A=0.0002, B=0.0003, and C=0.9642.

In view of the functional relationship presented above, an additional aspect of the first and second embodiments is a composition comprising a sulfomethylated polymyxin having viscosity values as determined by the above-mentioned quadratic expression.

Example 4 and 5 demonstrate how two CMS compositions were tested in a Next Generation Impactor (NGI). One was 20% w/v CMS (85 mg A/mL) and the other was 26.4 w/v CMS (112.5 mg A/mL). Both delivered good sprays and would be useful in inhalation treatment of lung related infections. The air flow used in the assessment was 15 L/min. The MMAD varied from approx. 6.5 to 8 microns and the Fine Particle Mass is approx. around 4 to 6 mg CMS per inhalation (50 micro liter). The FPM is considered to be the fraction of the aerosol that potentially can reach the lungs. This is the fraction able to be deposited in the lungs; usually stage 2-7. A treatment could consist of anything from 1 to 10 inhalations, 1 to 2 times daily. The NGI assessment clearly shows that the aqueous Metered-Dose Inhaler is a preferred inhalation device, and the only type of device capable of utilizing the preferred container for the highly concentrated CMS solutions. The potential benefit from using a solution is a better tolerance of inhaled solution compared to inhalation of dry powders which normally provokes coughing.

A Function Acceptance Test (FAT) was employed using a Universal Induction Port (UPI) that simulates the throat in standard in the NGI measurements.

The NGI has seven stages plus a Micro-Orifice Collector (MOC). At a volumetric flow rate of 60 L/Min, the cut-off points for stages 1 to 7 are 8.06, 4.46, 2.82, 1.66, 0.94, 0.55 and 0.34 microns respectively. At 15 liters per minute it is slightly different.

Example 4

An aqueous solution comprising 20% w/v (85 mg A/mL) colistimethate sodium (CMS) was aerosolized by an aqueous Metered-Dose Inhaler comprising a spray nozzle unit having orifice diameter of 1.8 μm and a 35 bar powerpack. The airflow was 15 L/min.

Figure 2:
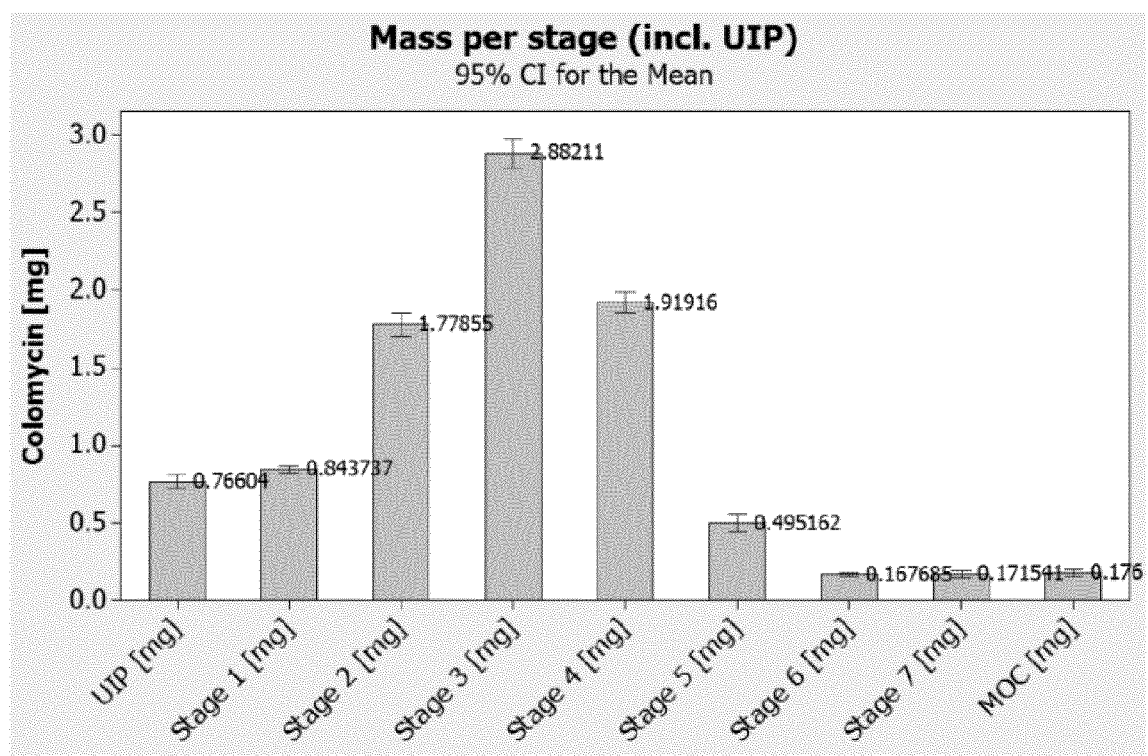
FIG. 2. Mass amount of the Example 4 composition delivered per stage, including universal induction port ("UIP").

The interval plot of the Example 4 composition is depicted in FIG. 1. There, it can be seen that the MMAD for the composition is 6.6 μm with an associated experimental variance. The mass amount of the Example 4 composition delivered per stage, including universal induction port ("UIP") is illustrated in FIG. 2. The amount delivered during each stage is shown in the following table.

| Stage | Mass of CMS per stage, mg |
|---|---|
| UIP | 0.77 |
| 1 | 0.84 |
| 2 | 1.78 |
| 3 | 2.88 |
| 4 | 1.92 |
| 5 | 0.50 |
| 6 | 0.17 |
| 7 | 0.17 |
| MOC | 0.18 |

Figure 3:
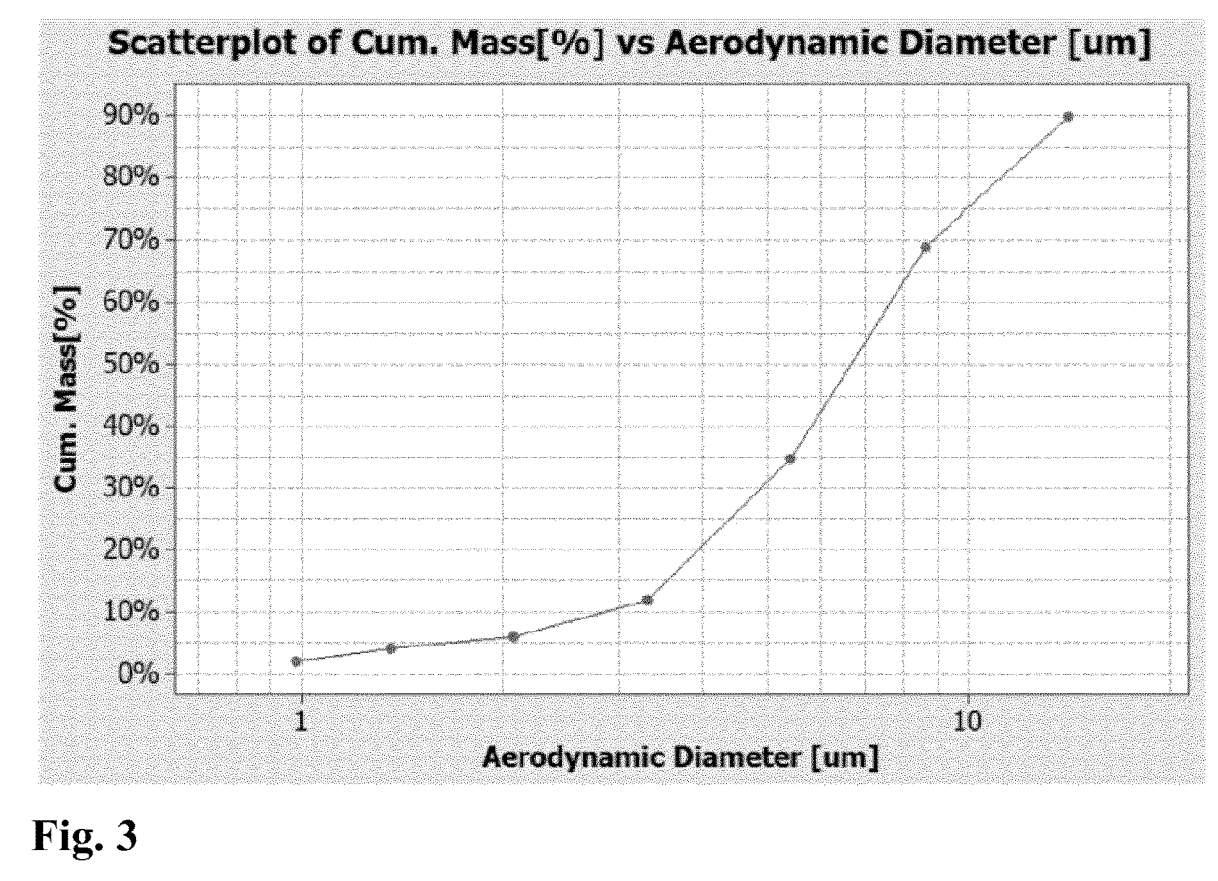

From this data, it can be seen that the maximum amount of CMS is delivered in the third stage. A scatterplot of the cumulative mass (%) vs. aerodynamic diameter (in μm) for Example 4 composition is depicted in FIG. 3.

Example 5

An aqueous solution comprising 26% w/v (112.5 mg A/mL) colistimethate sodium (CMS) was aerosolized by two different aqueous Metered-Dose Inhalers comprising a spray nozzle unit having orifice diameter of ca 1.9 μm and a 43.8 bar powerpack and a 34.5 bar powerpack respectively. The airflow was 15 L/min.

Figure 4:
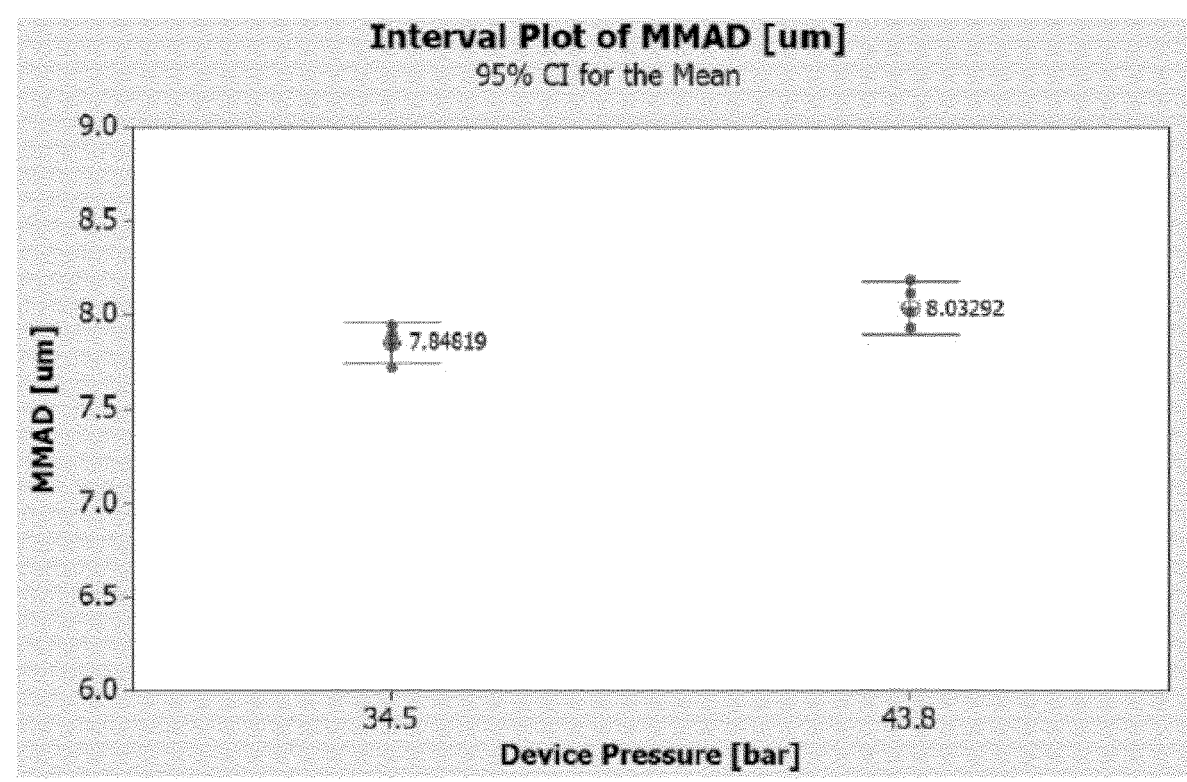
FIG. 4. Interval plot of mass median aerodynamic diameter (μm) of the Example 5 composition at two different pressures.

An interval plot of mass median aerodynamic diameter (μm) of the Example 5 composition at two different pressures is depicted in FIG. 4.

Figure 5:
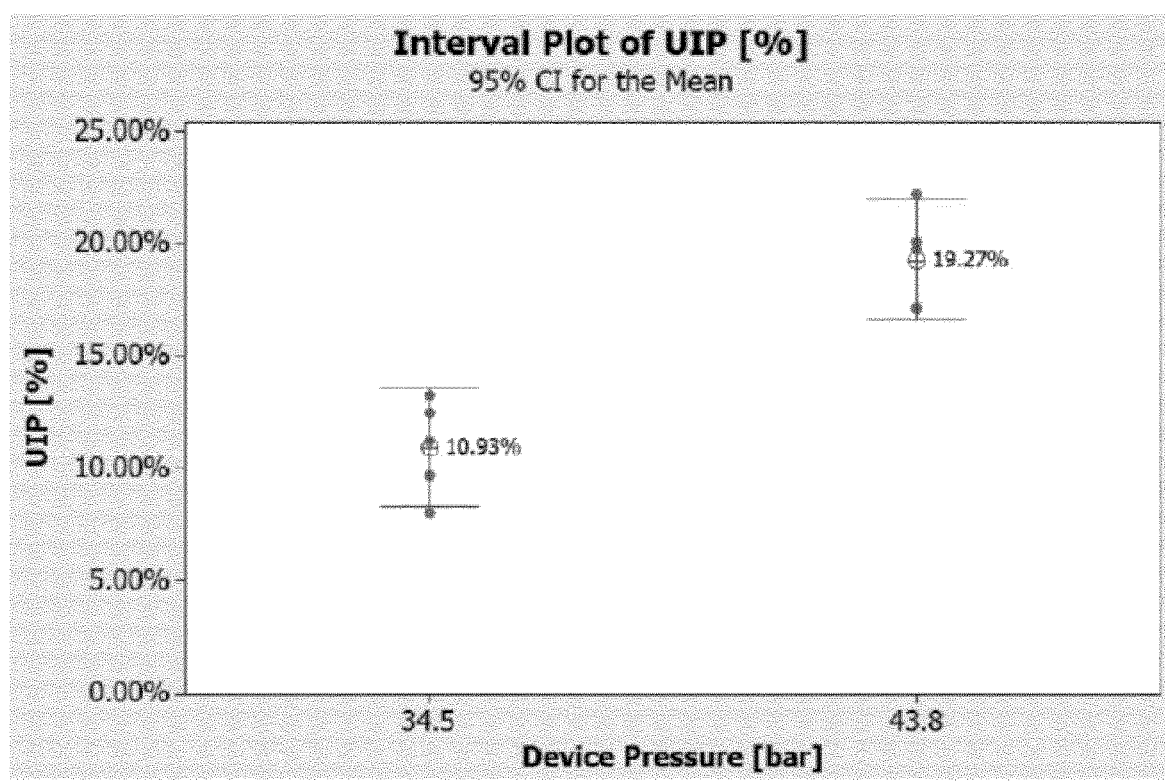
FIG. 5. An interval plot of the UIP (%) for two separate pressures for the Example 5 composition at two different pressures.

An interval plot of the UIP (%) for two separate pressures for the Example 5 composition is depicted in FIG. 5.

Figure 6:
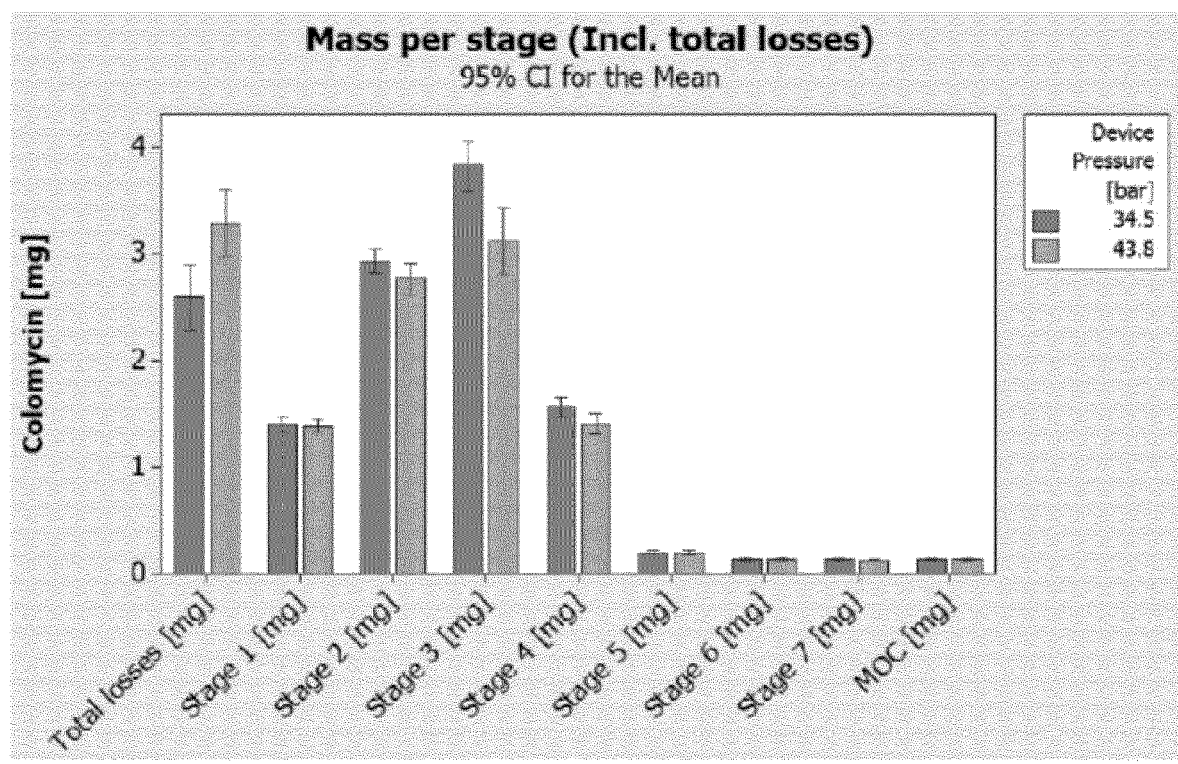
FIG. 6. Scatterplot of cumulative mass (%) vs. aerodynamic diameter for Example 5 composition at two different pressures.

The mass amount of the Example 5 composition, per stage, for the two pressures is depicted in FIG. 6.

Figure 7:
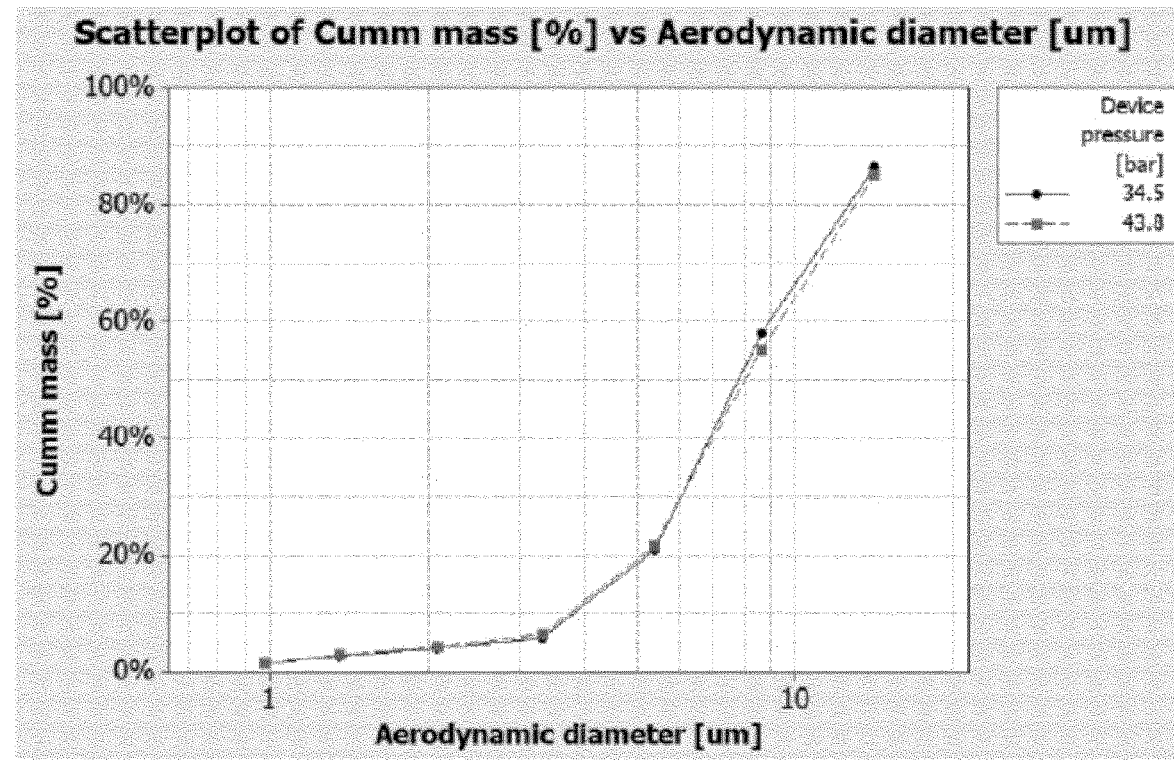
FIG. 7. Scatterplot of cumulative mass (%) vs. aerodynamic diameter for Example 5 composition at two different pressures.

A scatterplot of cumulative mass (%) vs. aerodynamic diameter for Example 5 composition, at two different pressures, is depicted in FIG. 7.

Example 6

Two aqueous solutions comprising 85 mg A/ml and 94 mg A/ml colistimethate sodium (CMS) were aerosolized by an aqueous Metered-Dose Inhaler comprising a spray nozzle unit having orifice diameter of ca 1.8 μm, a 38 bar powerpack and a 2 μm sieve.

The actuation time, mouth piece deposition, fine particle fraction etc. was measured as indicated in the following tables:

| | | | | 85 mg A/ml CMS: | | | | |
|---|---|---|---|---|---|---|---|---|
| Device | Airflow [L/min] | Actuation Time [s] | Mouth-Piece [%] | Medium OPC [%] | Stage 1 - 8 [mg] | Stage 2 - 8 [mg] | Stage 3 - 8 [mg] | FPD 11 um [mg] |
| 1 | 15 | 5.40 | 8.19% | 12.89% | 7.4 | 6.7 | 5.3 | 6.3 |
| | 20 | 5.41 | 10.53 | 12.47% | 7.2 | 6.6 | 4.9 | 6.3 |
| 2 | 15 | 4.72 | 5.26% | 13.15% | 7.6 | 6.7 | 4.8 | 6.1 |
| | 20 | 4.77 | 6.78% | 15.27% | 7.4 | 6.6 | 4.5 | 6.3 |
| 3 | 15 | 4.69 | 6.07% | 13.73% | 7.3 | 6.5 | 4.7 | 5.9 |
| | 20 | 4.67 | 6.78% | 20.14% | 6.5 | 5.9 | 4.0 | 5.6 |
| Average | 15 | 4.94 | 6.51% | 13.26% | 7.5 | 6.6 | 4.9 | 6.1 |
| | 20 | | 8.86% | 15.93% | 7.0 | 6.4 | 4.5 | 6.1 |

| | | | 94 mg A/ml CMS: | | | | |
|---|---|---|---|---|---|---|---|
| Device | Airflow [L/min] | Actuation Time [s] | Mouth-Piece [%] | Medium OPC [%] | Stage 1 - 8 [mg] | Stage 2 - 8 [mg] | Stage 3 - 8 [mg] | FPD 11 um [mg] |
| 1 | 15 | 4.72 | 7.78% | 13.99% | 7.9 | 7.1 | 5.3 | 6.5 |
|   | 20 | 4.81 | 10.70% | 14.56% | 7.7 | 6.9 | 4.9 | 6.6 |
| 2 | 15 | 4.97 | 8.52% | 15.20% | 7.9 | 6.9 | 4.8 | 6.2 |
|   | 20 | 5.00 | 7.45% | 18.24% | 7.7 | 6.8 | 4.3 | 6.4 |
| 3 | 15 | 4.91 | 6.00% | 16.45% | 8.1 | 7.0 | 4.9 | 6.3 |
|   | 20 | 4.93 | 7.82% | 19.08% | 7.9 | 7.0 | 4.4 | 6.5 |
| Average | 15 | 4.89 | 7.43% | 15.21% | 8.0 | 7.0 | 5.0 | 6.3 |
|   | 20 |  | 8.82% | 17.08% | 7.8 | 6.9 | 4.6 | 6.5 |

Figure 8:
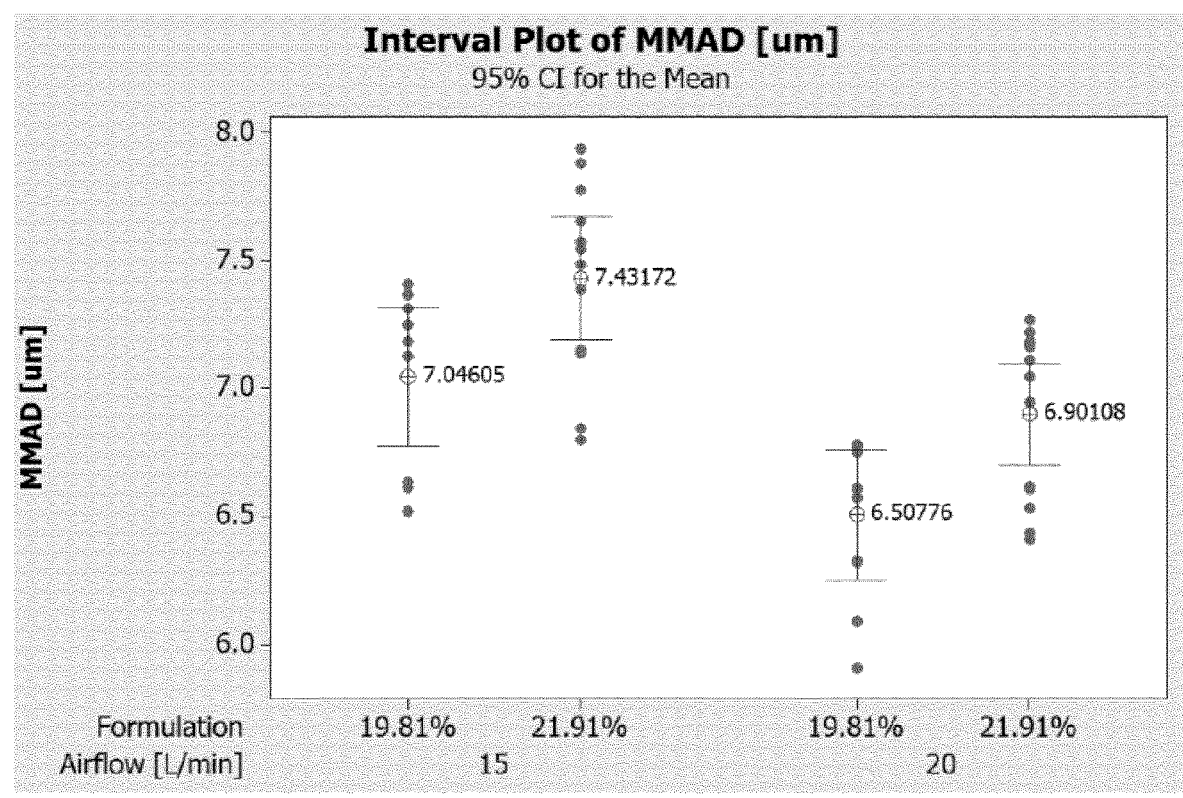
FIG. 8. Interval plot of mass median aerodynamic diameter (μm) of the Example 6 composition at two different pressures.

An interval plot of mass median aerodynamic diameter (μm) of the Example 6 compositions at two different flow rates is depicted in FIG. 8.

Example 7

An aqueous solution comprising 94 mg A/ml colistimethate sodium (CMS) was aerosolized by an aqueous Metered-Dose Inhaler comprising a spray nozzle unit having orifice diameter of ca 1.9 μm, a ca 38 bar powerpack and a 2 μm sieve. The actuation time, mouth piece deposition, fine particle fraction etc. was measured after 10 actuations followed by approximately 17 hours storage before the next 10 actuations as indicated in the following table:

| Device | Airflow [L/min] | Moment | Actuation time [s] | Mouthpiece [%, mg] | | Medium OPC [%, mg] | | Fraction passed throat [%, mg] | | FPD 11 um [%, mg] | |
|---|---|---|---|---|---|---|---|---|---|---|---|
| 1 | 15 | afternoon | 4.91 | 6% | 7.1 | 23% | 26.1 | 71% | 80.9 | 75% | 60.7 |
|   |    | next mornging | 6.11 | 7% | 7.2 | 19% | 20.1 | 75% | 84.0 | 78% | 65.4 |
| 2 |    | afternoon | 4.53 | 6% | 6.8 | 21% | 23.7 | 73% | 82.3 | 76% | 62.2 |
|   |    | next morning | 4.92 | 5% | 5.7 | 22% | 24.2 | 73% | 82.2 | 76% | 62.0 |
| 3 | 20 | afternoon | 4.36 | 7% | 8.4 | 19% | 20.0 | 74% | 84.4 | 82% | 68.8 |
|   |    | next morning | 4.58 | 7% | 8.1 | 16% | 18.8 | 77% | 88.2 | 84% | 74.4 |
| 4 |    | afternoon | 4.41 | 7% | 8.1 | 19% | 22.4 | 74% | 85.6 | 80% | 68.5 |
|   |    | next morning | 4.49 | 8% | 9.1 | 22% | 24.4 | 71% | 80.1 | 80% | 63.9 |

Figure 9:
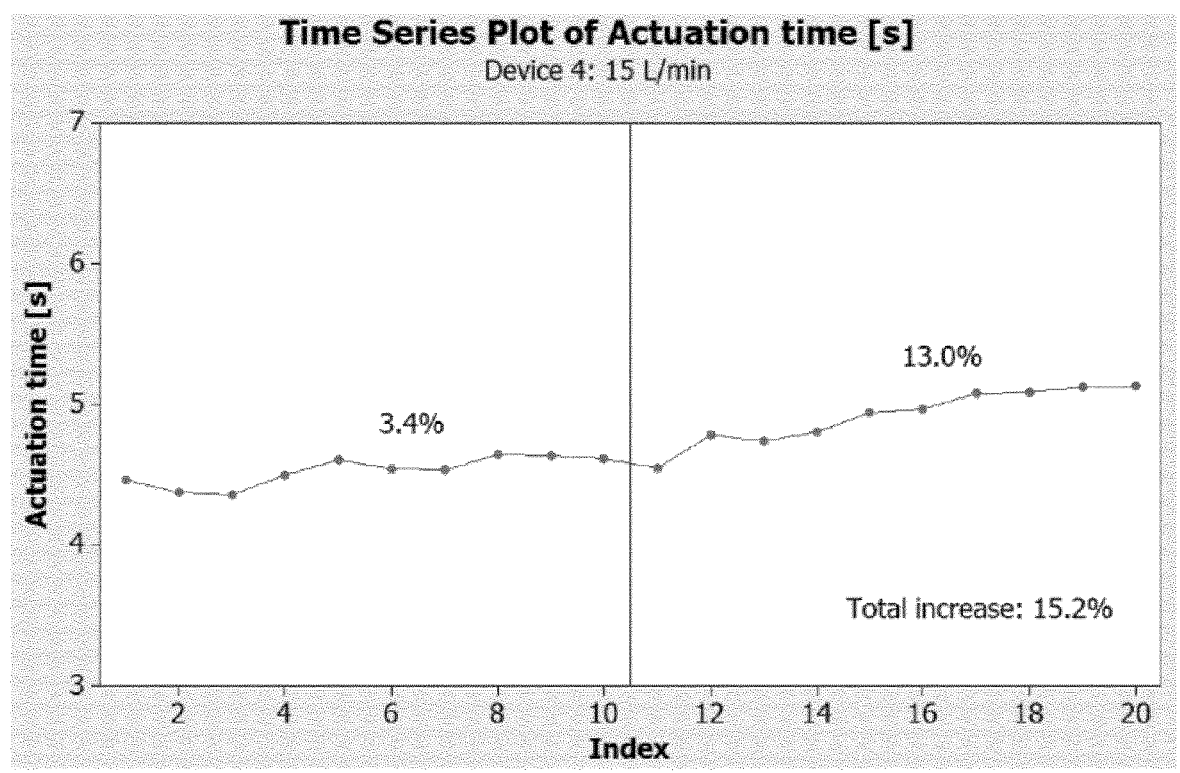
FIG. 9. Time series plot of actuation time for device no 4 during 10 actuations followed by storage for 17 hours at room temperature and then further 10 actuations. The data were collected from the experiment disclosed in example 7.
Figure 10:
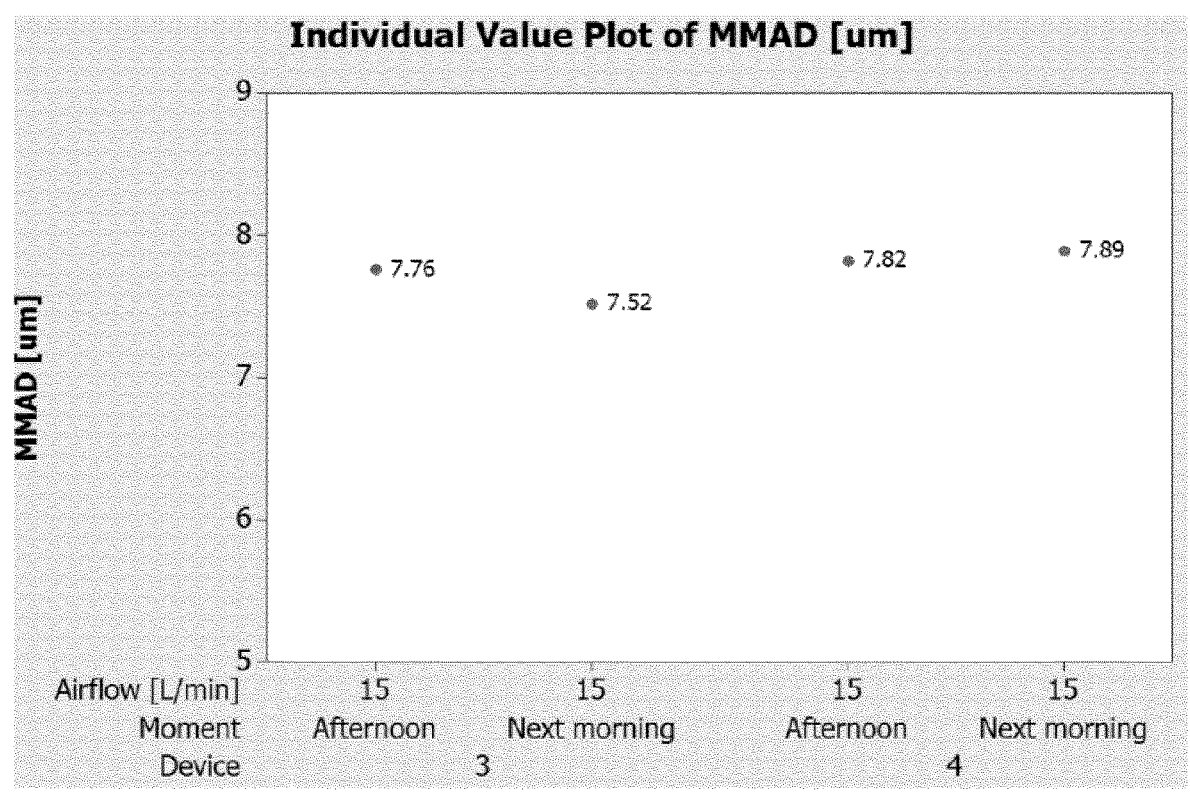
FIG. 10 Individual Value plot of MMAD for device no 3 and device no 4 before and after storage for 17 hours at room temperature. The data were collected from the experiment disclosed in example 7.
Figure 11:
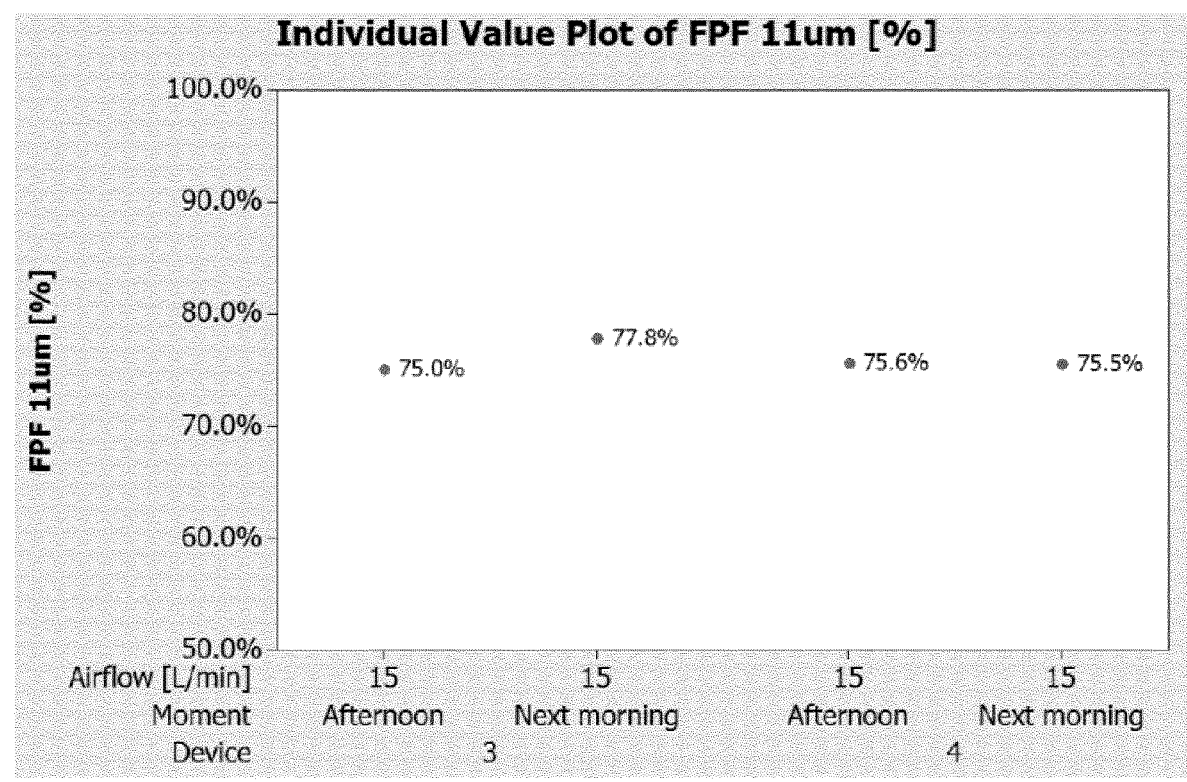
FIG. 11. Individual Value Plot of the Fine particle fraction (FPF) 11 microns for device no 3 and device no 4 before and after storage for 17 hours at room temperature. The data were collected from the experiment disclosed in example 7.
Figure 12:
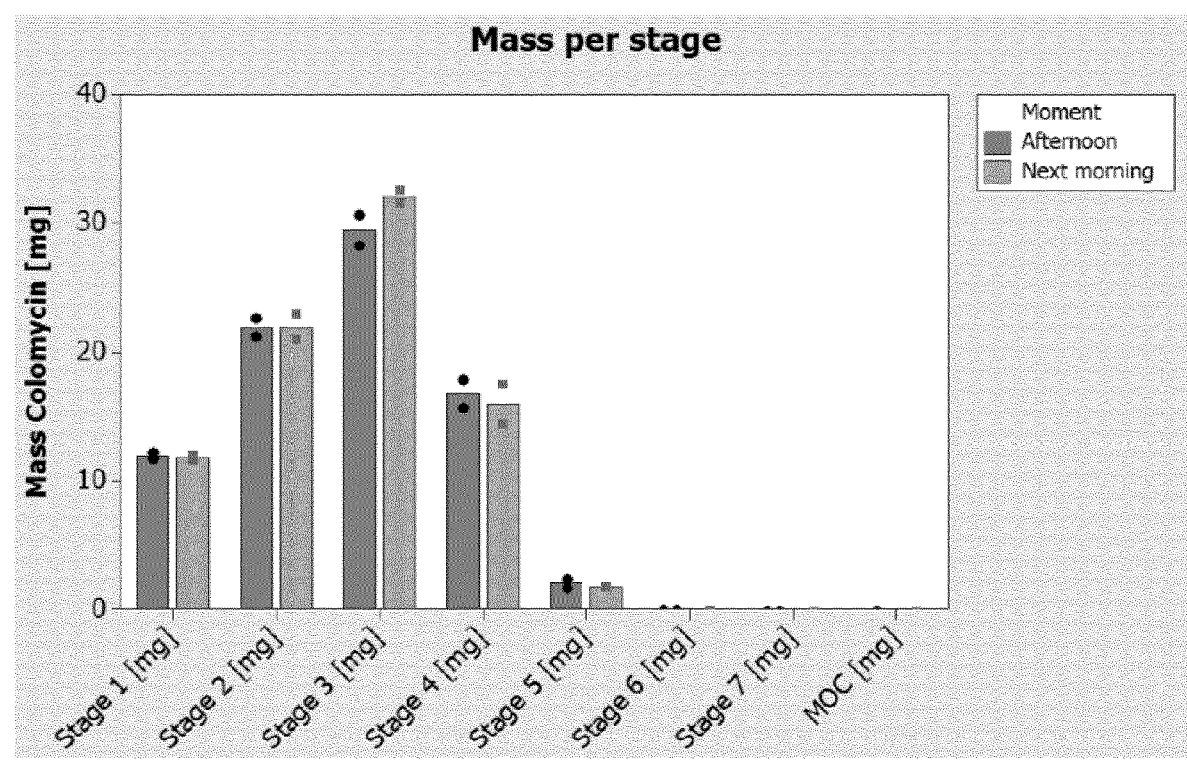
FIG. 12. Mass per stage distribution for device no 3 and device no 4 before and after storage for 17 hours at room temperature. The data were collected from the experiment disclosed in example 7.

FIG. 9 shows how the actuation time increases during use and after 17 hours storage at room temperature of the device no 4. FIG. 10 shows the MMAD during use of device no 3 and 4. FIG. 11 shows the FPF during use.

Although a full and complete description is believed to be contained herein, certain patent and non-patent references, including the above-mentioned USP and Ph. Eur. Monographs, may include certain essential subject matter. To the extent that these patent and non-patent references describe essential subject matter, these references are hereby incorporated by reference in their entirety. It is understood that the meanings of the incorporated subject matter are subservient to the meanings of the subject matter disclosed herein.

The invention claimed is:

1. A pulmonary administration device, comprising
   a spray nozzle unit and
   a cartridge containing an aqueous solution comprising from 80 to 400 mg A/mL of a sulfomethylated polymyxin,
   wherein the solution is free from visible particles after storage for 3 months at 25° C.

2. The device according to claim 1, wherein the sulfomethylated polymyxin is colistimethate sodium.

3. The device according to claim 2, wherein the concentration of the colistimethate sodium ranges from 80 to 120 mg A/mL.

4. The device according to claim 2, wherein the concentration of the colistimethate sodium ranges from 85 to 113 mg A/mL.

5. The device according to claim 2, wherein the cartridge has a nominal volume of 0.5-1.5 mL.

6. The device according to claim 1, wherein the concentration of the sulfomethylated polymyxin ranges from 80 to 200 mg A/mL.

7. A method for pulmonary administration in a patient in need thereof, comprising
   actuating an inhaler comprising a spray nozzle unit and a cartridge containing an aqueous solution comprising from 70 to 400 mg A/mL of a sulfomethylated polymyxin; and
   administering the aqueous solution to the patient in the form of droplets having a mass median aerodynamic diameter of from 4 to 8 μm.

8. The method of claim 7, wherein the droplets have a mass median aerodynamic diameter of from 5.5 to 7.5 μm.

9. The method according to claim 7, wherein the sulfomethylated polymyxin is colistimethate sodium.

10. The method according to claim 9, wherein the aqueous solution comprises from 80 to 120 mg A/mL of colistimethate sodium.

11. The method according to claim 10, wherein the aqueous solution comprises from 85 to 113 mg A/mL of colistimethate sodium.

12. The method according to claim 10, wherein the patient suffers from chronic lung disorder.

13. The method according to claim 12, wherein the chronic lung disorder is selected from among asthma, cystic fibrosis (CF), non-CF bronchiectasis, a chronic obstructive pulmonary disease, or a combination thereof.

14. The method according to claim 7, wherein the spray nozzle unit has orifices with a diameter of from 1.5 to 2.2 μm.

15. The method according to claim 7, wherein the patient is infected with a Gram negative bacteria.

16. The method according to claim 15, wherein the Gram negative bacteria is *Enterobacter aerogenes, Escherichia coli, Klebsiella pneumoniae, Pseudomonas aeruginosa*, or a combination thereof.

17. A method for pulmonary administration in a patient in need thereof, comprising
   actuating an inhaler comprising a spray nozzle unit having an orifice diameter of 1.7-2.0 μm and a cartridge containing an aqueous solution comprising from 90 to 100 mg A/mL of colistimethate sodium; and
   administering the aqueous solution to the patient in the form of droplets having a mass median aerodynamic diameter of from 4 to 8 μm with an airflow of 15-20 L/min.

* * * * *